United States Patent [19]

Shepherd

[11] 4,230,628
[45] Oct. 28, 1980

[54] 4-[(CARBOXYL- AND SULFAMYL-SUBSTITUTED ALKYL)-AMINO] BENZOIC ACIDS AND ANALOGS

[75] Inventor: Robert G. Shepherd, South Nyack, N.Y.

[73] Assignee: American Cyanamid Company, Stamford, Conn.

[21] Appl. No.: 895,574

[22] Filed: Apr. 12, 1978

[51] Int. Cl.$^3$ .................. C07C 101/44; C61K 31/245
[52] U.S. Cl. ................... 260/404; 260/404.5; 260/326.85; 260/345.8 R; 260/348.43; 260/348.44; 260/397.7 R; 260/465 D; 260/500.5 H; 260/558 A; 260/508; 544/162; 546/226; 548/341; 548/201; 560/12; 560/37; 560/43; 560/44; 562/430; 562/439; 562/458; 424/263; 424/278; 424/283; 424/269; 424/310; 424/319; 424/321; 424/324; 564/162; 260/453RW
[58] Field of Search ................ 562/458; 560/44; 260/404; 260/404.5

[56] References Cited

U.S. PATENT DOCUMENTS 3,766,260  10/1973  Carney et al. ................ 260/404
3,868,416  2/1975  Albright et al. .............. 562/458

OTHER PUBLICATIONS

Rating et al., Chem. Absts., 73, 57295(m) (1970).
Kosolapoff, Chem. Absts., 60, 1729(a) (1964).
Bykou et al. Chem. Absts., 59, 4067(g) (1963).

*Primary Examiner*—G. T. Breitenstein
*Attorney, Agent, or Firm*—Robert P. Raymond

[57] ABSTRACT

This disclosure describes novel 4-[(carboxyl- and sulfamyl-substituted alkyl)amino]benzoic acids and analogs which are useful as hypolipidemic and antiatherosclerotic agents.

5 Claims, No Drawings

4-[(CARBOXYL- AND SULFAMYL-SUBSTITUTED ALKYL)-AMINO] BENZOIC ACIDS AND ANALOGS

BRIEF SUMMARY OF THE INVENTION

This invention relates to new organic compounds and, more particularly, is concerned with 4-[(carboxyl- or sulfamyl-substituted alkyl)amino]benzoic acids and analogs which may be represented by the following structural formula:

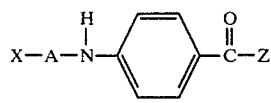

wherein X is selected from the group consisting of carboxy, loweralkoxycarbonyl, aryloxycarbonyl, heteroaryloxycarbonyl, carbamyl, mono- or diloweralkylcarbamyl, cyano, sulfo, monoalkyl- or monoarylsulfamyl; A is an unbranched or branched alkylene group, optionally saturated or mono- or polyunsaturated, and containing or not containing a cycloalkyl group, represented by the formula $C_nH_{2(n-p)}$ with n being an integer from 1 to 18, inclusive, and p being an integer from 0 to 5, inclusive; and Z is selected from the group consisting of hydrogen, hydroxy, loweralkoxy, loweralkoxyalkoxy, diloweralkylaminoalkoxy, (mono- or polyhydroxy)loweralkoxy, allyloxy, 2,3-epoxypropoxy, substituted or unsubstituted(benzyloxy, phenoxy, or pyridylmethoxy), 3-pyridyloxy, mono- or poly-(carboxyloweralkoxy or carboxyhydroxyloweralkoxy), tetrahydropyranyloxy, (mono- or polyhydroxy)alkylamino, allylamino, propargylamino, 2-sulfoethylamino, (mono- or polycarboxy)loweralkylamino, (mono- or polycarbalkoxy)loweralkylamino, loweralkanoylamino, (substituted or unsubstituted aroyl)amino, loweralkanesulfonylamino, (substituted or unsubstituted arene)sulfonylamino, loweralkanoylhydrazino, hydroxylamino, polymethyleneimino, and 4-carboethoxy- or 4-carboxythiazolidino; with the proviso that when X is a carbamyl, cyano or sulfo group, X and the nitrogen atom in Formula I may not be bonded to the same carbon atom of the group A; and the pharmaceutically acceptable non-toxic acid-addition and cationic salts thereof. Lower whenever applied to alkyl or alkoxy refers to a chain of 1–4 carbon atoms which may be branched or unbranched. The polyhydroxy, polycarboxy and polycarbalkoxy groups referred to above contain 2 to 4 hydroxy, carboxy or carbalkoxy groups, respectively.

Suitable groups contemplated by the present invention for the substituent X are, for example, carbomethoxy, carboethoxy, carbo-tert-butoxy, carbophenoxy, carbo-p-chlorophenoxy, carbo-4-pyridylmethoxy, carbo-3-pyridyloxy, N-methylcarbamyl, N,N-diethylcarbamyl, N-methylsulfamyl, N-phenylsulfamyl, N-(p-toluene)sulfamyl, and the like.

Suitable alkylene, alkenylene, alkynylene, and cycloalkylene groups contemplated by the present invention for the moiety A are, for example, octamethylene, undecamethylene, tetradecamethylene, hexadecamethylene, 3-methylheptamethylene, 1,1,6-trimethylheptamethylene, 1-(n-butyl)pentamethylene, 1-ethyl-1-methylpentamethylene, 2,7-dimethyloctamethylene, 1-(n-octyl)decamethylene, 2-undecenylene, 1-(2-butenyl)decamethylene, 1-(1-methyl-2-propenyl)decamethylene, 1-(n-hexyl)-3-decenylene, 7-hexadecenylene, 9-hexadecenylene, 1-(n-butyl)-3-dodecenylene, 12-hexadecenylene, 3,7,7-trimethyl-2-heptenylene, 1-(n-propyl)-2-heptenylene, 2-decenylene, 9-methyl-2-nonenylene, 1-(n-pentyl)-2-undecynylene, 1-ethyl-2-tridecynylene, 1-(n-hexyl)-4-decynylene, 4-hexadecynylene, 2,6,6-trimethyl-1,3-cyclohexylenemethylene, 2,2,4-trimethyl-1,3-cyclopentylenemethylene, and the like.

Suitable groups contemplated by the present invention for the substituent Z are, for example, methoxy, isopropoxy, 2-ethoxyethoxy, 2-dimethylaminoethoxy, 1-methyl-4-piperidyloxy, 4-pyridylmethoxy, 2,3-dihydroxypropoxy, 2-hydroxypropoxy, 3-hydroxypropoxy, 4-chlorobenzyloxy, 3-methylbenzyloxy, 4-fluorophenoxy, 4-sulfophenoxy, 2,6-dichlorophenoxy, 3-carboxyphenoxy, 2,6-dimethyl-3-pyridyloxy, 6-methoxy-3-pyridyloxy, 2-hydroxy-3-pyridyloxy, 5-carboxy-3-pyridyloxy, carboxymethoxy, 1-methoxycarbonylpropoxy, 2-methoxycarbonyl-2-propoxy, 2,3-dihydroxypropylamino, carboxymethylamino, acetylamino, benzoylamino, 4-chlorobenzoylamino, methanesulfonylamino, p-toluenesulfonylamino, 1-piperidyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel 4-[(carboxyl- and sulfonyl-substituted alkyl)amino]benzoic acids and analogs of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said esters.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study crried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of the invention are new and novel 4-[(carboxyl- and sulfamyl-substituted alkyl)amino]benzoic acids and analogs which have therapeutically useful biological and pharmacological properties. No hypolipemic activity has been reported in the literature for these compounds and they are different in structure and superior in action to other hypolipemic agents. The compounds of this invention lower serum-lipid concentration and also decrease the deposition of lipids in the aorta. The novel compounds of this invention are reliably absorbed from the gastrointestinal tract and cause little, if any gastrointesinal irritation. 4-Alkylaminobenzoic acids and esters thereof are described in our U.S. Pat. No. 3,868,416.

We have now found that certain members of this class of compound can safely and effectively lower both serum sterols and triglycerides in warm-blooded mammals. Such actions on serum-lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosyntheses and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The 4-[(carboxy- and sulfamyl-substituted alkyl)amino]benzoic acids and analogs of the present invention are, in general, white crystalline solids having characteristic melting points and absorption spectra. They are soluble in organic solvents such as lower alkanols, chloroform, toluene, dimethylformamide, and the like but are generally not very soluble in water.

The novel 4-[(carboxy- and sulfamyl-substituted alkyl)amino]benzoic acids and analogs of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like. The compounds which contain acidic groups form pharmaceutically acceptable salts with bases such as the alkali metals, the alkaline earths, and the like.

Many of the novel 4-[(carboxy- and sulfamyl-substituted alkyl)amino]benzoic acids, esters and amides of the present invention are prepared by alkylation of a 4-aminobenzoic acid, ester, or amide with the appropriate alkylating agent followed, if necessary, by chemical transformation of the substituent on the alkylamino group. Alkylating agents especially for these reactions include haloalkanoic acids, esters, and amides; haloalkanesulfonic acids and amides; and haloalkanonitriles. Many of these alkyalting agents are obained from the corresponding hydroxy compounds, for example, the reaction of 16-hydroxyhexadecanoic acid with hydrogen bromide affords 16-bromohexadecanoic acid. In other cases, these alkylating agents are obtained from the haloalcohols, for example, the reaction of 11-bromoundecanol with potassium cyanide affords 11-hydroxyundecanonitrile which in turn is converted to 11-bromoundecanonitrile by reaction with hydrogen bromide. Similarly, the reaction of 11-bromoundecanol with sodium sulfite yields 11-hydroxyundecanesulfonic acid which is converted to 11-bromoundecanesulfonic acid by reaction with hydrogen bromide. Other haloalkanesulfonic acids are prepared from the corresponding mercaptans, for example, oxidation of 6-bromohexanethiol (obtained by reaction of 6-bromo-1-methanesulfonyloxyhexane with potassium thioacetate followed by hydrolysis with sodium hydroxide) with nitric acid affords 6-bromohexanesulfonic acid. Still other haloalkanesulfonic acids are prepared by the addition of bisulfite salts to olefins in the presence of free-radical initiators. An example of this type of rection is the addition of sodium bisulfite to 8-bromo-1-octene in the presence of dibenzoyl peroxide to yield 8-bromooctanesulfonic acid. These carboxylic and sulfonic acids may be converted to the desired amides or esters by conventional methods. The compounds of this invention are also obtained by addition of ethyl p-aminobenzoate to $\omega$-unsaturated alkanoic acids, amides or esters such as crotonic acid, ethyl acrylate, and 2-hexenoic amide and to ω-unsaturated alkanesulfonic acids or amides such as ethylenesulfonic acid and 2-butylenesulfonamide.

The alkylation of 4-aminophenyl compounds is carried out with the above metnioned halides or alternatively with methanesulfonates, tosylates, trifluoromethanesulfonates or the like with or without solvent at 50° C.-150° C. Suitable solvents are loweralkanols, chloroform, N,N-dimethylformamide, N,N-dimethylacetamide, diglyme, dimethylsulfoxide, acetonitrile, toluene, benzene, hexamethylphosphoramide and the like. The reaction may be carried out with an equivalent of base such as an alkali carbonate or bicarbonate, or with a catalytic amount of copper powder when alkyl halides are used as the alkylating agent. Alternatively, alkylation of the sodium salt (formed with sodium hydride) of either the amino group of a 4-aminophenyl compound or the anilide moiety of a 4-(acetylamino)-phenyl compound yields the desired alkylation product or an N-acetyl derivative thereof. Other 4-aminophenyl compounds useful in these alkylation reactions, or in the subsequently described acylation reactions, are for example, 4-aminobenzonitrile, p-toluidine, and the acetal of 4-aminobenzaldehyde. In these cases, the desired alkylation product is obtained by a subsequent oxidative or hydrolytic transformation of the methyl, nitrile, or acetal group.

Two types of substitution reactions also yield the 4-(substituted-alkyl amino)benzoate esters, firstly, reaction of esters of 3,4-didehydrobenzoic acid with a (substituted-alkyl)amine (or its alkali metal salt). Friedel-Crafts acylation of an N-(substituted-alkyl)aniline or N-acyl-N-(substituted alkyl)aniline yields certain intermediates thereto. The former type of reaction is carried out by treating a 4-halobenzoate ester such as phenyl 4-bromobenzoate with the lithium, potassium or sodium salt of an alkylamine such as 16-carboethoxyhexadecylamine in diethyl ether or other aprotic solvent. The second method comprises reacting 16-carboethoxyhexadecylaniline and the like or its N-acetyl derivative with a carboalkoxy chloride and anhydrous aluminum chloride in dry diethyl ether, halocarbon or hydrocarbon medium.

The 4-[(substituted-alkyl)amino]benzoic acids of the present invention may be obtained by hydrolysis of the corresponding esters or amides in boiling aqueous ethanolic alkali, followed by acidification. Alternatively, these benzoic acids may be isolated as their alkali metal salts.

Many of the novel compounds of the present invention which contain one or more acidic substituents may be converted to their organic or inorganic cationic salts for therapeutic use. The sodium or potassium salts which are formed in solution in the course of the above described hydrolysis reactions may be isolated as solids by cooling. When it is desirable to purify a compound in the form of the acid, the salt is conveniently formed afterward by treating a solution of the acid with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

The novel esters and amides of the present invention may readily be prepared by treating a derivative of the corresponding carboxylic acid, such as the acid halide, mixed acid anhydride or activated ester or amide with the appropriate alcohol or amine, respectively. These reactions may be carried out in an inert solvent at a temperature of 50°-125° C. for 30 minutes to 18 hours or more. In the case of the acid halide and other acid-forming acylating agents, the reaction is carried out in the presence of an acid scavenger such as diisopropylethylamine; 4-dimethylaminopyridine; pyridine, triethylamine; finely powdered sodium carbonate and the like. A protecting group on the amino nitrogen is used for best results. The simplest protecting group is provided by protonation of the amine to yield an anilinium salt prior to or during formation of the acylating form of the carboxyl group. Acylation of the amino group by carefully selected acyl groups such as carbobenzyloxy, carbo-t-butoxy, and trifluoroacetyl provides protection of this group from self-acylation during amide formation. These protecting groups are then removed by catalytic hydrogenation, mild acid treatment and mild alkali treatment, respectively. Other N-acyl protecting groups such as acetyl and succinoyl may be used and these are removed by conventional methods. Activated esters and amides, useful to synthesize the estes and amides of the prsent invention, are those containing carboxymethyl, 4-nitrophenyl, N-oxysuccinimide and 1-imidazolyl groups and the like. In certain cases, treatment of the acids with an excess of an appropriate hydroxy-containing substrate in the presence of a Lewis or mineral acid such as boron trifluoride, sulfuric acid or hydrochloric acid affords the corresponding esters. Ordinary esters such as the methyl and ethyl esters are sufficiently reactive to form the amides of the 4-[(substituted-alkyl)amino]benzoic acids and highly reactive amine substrates such as hydroxylamine, hydrazines and certain alkyl primary amines. In order to form amides from certain kinds of substrates, it is necessary first to form the alkali metal or strong organic base salts of these substrates prior to reacting them with the various aforementioned acylating forms of the 4-[(substituted-alkyl)amino]phenyl compounds. For example, aminoalkanecarboxylic and aminoalkanesulfonic acids are zwitterionic and must be converted to their salts, suitably in situ. They may also be used in the form of their esters and then hydrolyzed after amide formation. Certain substrates which are neutral, like the carboxamides, or slightly acidic, like the alkane or arene sulfonamides, are converted to acylatable sodium salts by reaction with sodium hydride or other basic reagents.

The carboxaldehydes of this invention may be prepared by several methods among which is alkylation of the corresponding acetal by the methods above followed by hydrolysis of the resulting 4-(substituted-amino)phenyl acetal to the aldehyde. Aldehydes may also be prepared by reduction of appropriate nitriles. For example, treatment of 4-(16-carboxyhexadecylamino)benzonitrile is conveniently carried out with diisobutyl aluminum hydride.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and anti-atherosclerotic efect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 50% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage-unit form should be pharmaceutically pure and substantially nontoxic in the amounts employed. In addition, the active ingredients may be incorporated into sustained-release preparations and formulations.

The invention will be described in greater detail in conjunction with the following specific Examples.

EXAMPLE 1

Preparation of 16-bromohexadecanoic acid

A mixture of 18 g. of 16-hydroxyhexadecanoic acid and 160 g. of 30-32% hydrogen bromide in acetic acid is treated with 32 ml. of concentrated sulfuric acid and stirred at ambient temperature for 18 hours. The solution is stirred under reflux for 7 hours and then poured into 500 ml. of ice-water and filtered. A methylene chloride solution of the product is treated with charcoal, dried over magnesium sulfate, and evaporated. Crystallization of the residue from ether-petroleum ether and then acetonitrile affords 16-bromohexadecanoic acid as a white solid.

EXAMPLE 2

Preparation of methyl 16-bromohexadecanoate

A mixture of 22 g. of 16-bromohexadecanoic acid and 200 ml. of methanol is treated with 1.0 ml. of concentrated sulfuric acid and stirred under reflux for 24 hours. The mixture is treated with 10 g. of sodium acetate and the solvent is evaporated. The residue is partially soluble in 300 ml. of ether and the mixture is filtered. The ether solution is dried over magnesium sulfate and evaporated. The residue is crystallized from petroleum ether to yield methyl 16-bromohexadecanoate as a white solid.

EXAMPLE 3

Preparation of 1(16-bromohexadecanoyl)pyrrolidine

A solution of 20 g. of 16-bromohexadecanoic acid and 27.5 ml. of thionyl chloride in 200 ml. of toluene is stirred under reflux for 5 hours and evaporated to a light yellow oil. A solution of the oil in 200 ml. of tetrahydrofuran is added dropwise with stirring to a solution of 10 g. of pyrrolidine in 200 ml. of tetrahydrofuran at 0° C. The mixture is filtered and the filtrate is evaporated. The residue is crystallized from petroleum ether to yield 1-(16-bromohexadecanoyl)pyrrolidine as a white solid.

EXAMPLE 4

Preparation of 12-hydroxydoecanonitrile

A solution 4.6 g. of 11-bromoundecanol and 1.6 g. of sodium cyanide in 40 ml. of dimethylformamide is heated at 80° C. for 18 hours, cooled, and poured into ice-water. The mixture is extracted with methylene chloride and the extract is dried over anhydrous magnesium sulfate. Evaporation of the solution affords 12-hydroxydodecanonitrile as a yellow oil.

EXAMPLE 5

Preparation of 12-(methanesulfonyloxy)dodecanonitrile

A solution of 15 g. of 12-hydroxydodecanonitrile and 14 ml. of triethylamine in 320 ml. of methylene chloride is stirred at 0° C. while 5.7 ml. of methanesulfonylchloride is added dropwise. The mixture is stirred at 0° C. for 1 hour, diluted with methylene chloride and extracted with water; cold, dilute hydrochloric acid; saturated aqueous sodium bicarbonate; and brine. The solution is dried over anhydrous magnesium sulfate and eaporated to yield 12-(methanesulfonyloxy)-dodecanonitrile as a yellow oil

EXAMPLE 6

Preparation of sodium 2-bromoethanesulfonate

A mixture of 6.2 g. of 1,2-dibromoethane, 12.5 ml. of ethanol and 4.5 ml. of water is stirred under reflux while a solution of 1.25 g. of anhydrous sodium sulfite in 4.5 ml. of water is added dropwise and for an additional 2 hours after the addition is completed. The mixture is evaporated and the residual solid is extracted with 20 ml. of boiling 95% ethanol, repeatedly. Crystallization from ethanol affords sodium 2-bromoethanesulfonate as a white solid.

EXAMPLE 7

Preparation of N-phenyl-2-bromoethanesulfonamide

A mixture of 10 g. of sodium 2-bromoethanesulfonate and 12 g. of finely powdered phosphorous pentachloride is heated on a steam bath until it liquefies and for 4 hours thereafter. The mixture is concentrated by distillation and the residue is extacted with chloroform. The extract is washed with water and 5% aqueous sodium bicarbonate solution, dried over calcium chloride and evaporated to yield a yellow oil.

A solution of the yellow oil in 100 ml. of tetrahydrofuran is added dropwise to a stirred solution of 18 g. of aniline in 150 ml. of tetrahydrofuran at 0° C. The mixture is filtered and the filtrate is evaporated. Crystallization of the residue from ether-petroleum ether yields N-phenyl-2-bromoethanesulfonamide as a white solid.

EXAMPLE 8

Preparation of ethyl 4(15-carbomethoxypentadecylamino)benzoate

A solution of 21 g. of methyl 16-bromohexadecanoate and 20 g. of ethyl 4-aminobenzoate in 150 ml. of hexamethylphosphoramide is stirred at 120° C. for 20 horus, cooled, diluted with water and filtered. A methylene chloride solution of the solid is dried over anhydrous magnesium sulfate, clarified with activated charcoal, and filtered through silica gel. The filtrate is evaporated and the residue crystallized from acetonitrile to yield ethyl 4-(15-carbomethoxypentadecylamino)benzoate as a white crystalline solid.

EXAMPLE 9

Preparation of 4-(15-carboxypentadecylamino)benzoic acid

A solution of 8.8 g. of ethyl 4-(15-carbomethoxypentadecylamino)benzoate, 4.5 g. of potassium hydroxide, and 10 ml. of water in 90 ml. of ethanol is stirred at 75° for 10 hours, cooled, diluted with water, brought to pH 4 with dilute hydrochloric acid, and filtered. The solid is dried and crystallized from acetic acid to yield 4-(15-carboxypentadecylamino)benzoic acid as a white crystalline solid.

EXAMPLE 10

Preparation of the disodium salt of 4(15-carboxypentadecylamino)benzoic acid

A solution of 4 g. of 4(15-carboxypentadecylamino)benzoic acid, 25 ml. of 1 N sodium hydroxide, and 75 ml. of water in 250 ml. of ethanol is formed by heating to reflux and then allowed to cool. The precipitate is collected by filtration and recrystallized from ethanol-water to yield the disodium salt of 4-(15-carboxypentadecylamino)benzoic acid as a white crystalline solid.

EXAMPLE 11

Preparation of ethyl 4-(15-carboxypentadecylamino)benzoate

A solution of 5 g. of ethyl 4-(15-carbomethoxypentadecylamino)benzoate and 0.8 g. of potassium hydroxide in 50 ml. of 95% ethanol is stirred at 50° C. for 10 hours, diluted with 100 ml. of water and acidified with concentrated hydrochloric acid. The solid is collected by filtration, dried, and recrystallized from toluene to yield ethyl 4-(15-carboxypentadecylamino)benzoate as a white solid.

EXAMPLE 12

Preparation of 4(15-carbomethoxypentadecylamino)benzonitrile

A solution of 12 g. of 4-aminobenzonitrile and 15 g. of methyl 16-bromohexadecanoate in 200 ml. of hexamethylphosphoramide is heated at 120° for 22 hours, allowed to cool, and diluted with water. The mixture is chilled and the precipitate which forms is collected, dried, and recrystallized from etherhexane to yield 4-(15-carbomethoxypentadecylamino)benzonitrile as a white solid.

EXAMPLE 13

Preparation of 4-(15-carboxypentadecylamino)benzonitrile

A solution of 3 g. of 4-(15-carbomethoxypentadecylamino)benzonitrile and 0.5 g. of potassium hydroxide in 50 ml. of 95% ethanol is stirred at 50° C. for 10 hours, diluted with water and acidified with dilute hydrochloric acid. The precipitate is collected, dried and recrystallized from ether-hexane to yield 4-(15-carboxypentadecylamino)benzonitrile as a white solid.

EXAMPLE 14

Preparation of 4-(15-carboxypentadecylamino)benzaldehyde

Di-iso-butylaluminum hydride (54 ml., 25% solution in toluene) is added with stirring to a solution of 5.1 g. of 4-(15-carboxypentadecylamino)benzonitrile under a nitrogen atmosphere. The temperature rises to 40° C. during the addition which takes 30 minutes and the reaction is then stirred for 1 hour. A solution of methanol in toluene (50 ml., 1:1) is added over 30 minutes and the mixture is poured into vigorously stirred ice-cold aqueous sulfuric acid (500 ml., 5%). After 10 minutes diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. Recrystallization from hexane affords 4-(15-carboxypentadecylamino)benzaldehyde as a white solid.

EXAMPLE 15

Preparation of ethyl 4-[2-(N-phenylsulfonamido)ethylamino]-benzoate

A solution of 7.1 g. of N-phenyl-2-bromoethanesulfonamide and 12.6 g. of ethyl 4-aminobenzoate in 100 ml. of hexamethylphosphoramide is stirred at 120° for 22 hours, cooled, diluted with water and filtered. The solid is dried and recrystallized from acetonitrile to yield ethyl 4-[2-(N-phenylsulfonamido)ethylamino]benzoate as a white solid.

Hydrolysis of the product by the method of Example 9 affords 4-[2-(N-phenylsulfonamido)ethylamino]benzoic acid.

EXAMPLE 16

Preparation of ethyl 4-(2-sulfoethylamino)benzoate

A solution of 4.1 g. of sodium 2-bromoethanesulfonate and 7.9 g. of ethyl 4-aminobenzoate in 110 ml. of hexamethylphosphoramide is stirred at 125° for 18 hours and then poured into dilute hydrochloric acid. The solid is collected by filtration, dried and recrystallized from acetonitrile to yield ethyl 4-(2-sulfoethylamino)benzoate as a white solid.

EXAMPLE 17

Preparation of 4-(2-sulfoethylamino)benzoic acid

A mixture of 4.4 g. of ethyl 4-(2-sulfoethylamino)benzoate, 2.3 g. of potassium hydroxide, 10 ml. of water, and 90 ml. of ethanol is stirred under reflux for 8 hours, allowed to cool, diluted with water, and brought to pH 4 with concentrated hydrochloric acid. The precipitate is collected by filtration, dried, and recrystallized from acetic acid to yield 4-(2-sulfoethylamino)benzoic acid as a white solid.

EXAMPLE 18

Preparation of 4-(15-carbomethoxypentadecylamino)benzoic acid

A mixture of 1.37 g. of 4-aminobenzoic acid, 3.50 g. of methyl 16-bromohexadecanoate, 2.12 g. of sodium carbonate and 140 ml. of hexamethylphosphoramide is stirred at 120° C. for 18 hours, allowed to cool, and poured into dilute hydrochloric acid. The precipitate is collected by filtration, dried, and crystallized from acetonitrile to yield 4-(15-carbomethoxypentadecylamino)benzoic acid as a white solid.

TABLE I

The 4[(substituted alkyl)amino]phenyl compounds shown in the Table were prepared by the methods of Examples 8 to 18. The requisite alkylating agents are prepared by the methods of Examples 1 to 8.

TABLE I

| Example No. | Method of Example | Compound |
|---|---|---|
| 19 | 8 | Ethyl 4-(3-carbomethoxyprop-2-enylamino)benzoate |
| 20 | 8 | Ethyl 4-(15-carbomethoxypentadec-4-ynylamino)benzoate |
| 21 | 9 | 4-[(3-Carboxy-2,4,4-trimethylcyclohexyl)amino]benzoic acid |
| 22 | 18 | 4-(13-Carbomethoxytridecylamino)benzoic acid |
| 23 | 9 | 4-(Carboxymethylamino)benzoic acid |
| 23a | 9 | 4-(3-Carboxypropylamino)benzoic acid |
| 24 | 8 | Ethyl 4-(1-carboethoxybutylamino)benzoate |
| 25 | 9 | 4-(5-Carboxypentylamino)benzoic acid |
| 25a | 9 | 4-(10-Carboxydecylamino)benzoic acid |
| 25 | 10 | Disodium salt of 4-(5-carboxypentylamino)benzoic acid |
| 26 | 11 | Ethyl 4-(10-carboxydecylamino)benzoate |
| 27 | 8 | Ethyl 4-(2-carboethoxyethylamino)benzoate |
| 27a | 8 | Ethyl 4-(3-carboxypropylamino)benzoate |
| 28 | 18 | 4-(10-Carbomethoxydecylamino)benzoic acid |
| 29 | 8 | Ethyl 4-(carboethoxymethylamino)benzoate |
| 30 | 10 | Disodium salt of 4-(1-carboxybutylamino)benzoic acid |
| 31 | 9 | 4-(2-Carboxyethylamino)benzoic acid |
| 32 | 8 | Ethyl 4-(3-carboethoxypropylamino)benzoate |
| 33 | 8 | Ethyl 4-(1-carboethoxyethylamino)benzoate |
| 34 | 8 | Ethyl 4-(5-carboethoxypentylamino)benzoate |
| 35 | 9 | 4-(Carboxymethylamino)benzoic acid |
| 36 | 9 | 4-(1-Carboxybutylamino)benzoic acid |
| 37 | 10 | Disodium salt of 4-(carboxymethylamino)benzoic acid |
| 38 | 10 | Disodium salt of 4-(10-carboxydecylamino)benzoic acid |
| 39 | 10 | Disodium salt of 4-(13-carboxytridecylamino)benzoic acid |
| 40 | 8 | Methyl 4-(carboethoxymethylamino)benzoate |
| 41 | 11 | Ethyl 4-(13-carboxytridecylamino)benzoate |
| 42 | 11 | Ethyl 4-(carboxymethylamino)benzoate |
| 43 | 11 | Ethyl 4-(5-carboxypentylamino)benzoate |
| 44 | 18 | 4-(Carbomethoxymethylamino)benzoic acid |
| 44a | 18 | 4-(Carboethoxymethylamino)benzoic acid |
| 45 | 18 | 4-(5-Carbomethoxypentylamino)benzoic acid |
| 46 | 18 | 4-(1-Carbomethoybutylamino)benzoic acid |
| 47 | 11 | Ethyl 4-(18-carboxyoctadecylamino)benzoate |
| 48 | 9 | 4-(4-Carboxybutylamino)benzoic acid |
| 49 | 10 | Sodium 4-(5-carbomethoxypentylamino)benzoate |
| 49a | 10 | Sodium 4-(5-carboethoxypentylamino)benzoate |
| 50 | 12, 13 | 4-(10-Carbomethoxydecylamino)benzaldehyde |
| 51 | 12, 13, 14 | 4-(2-Carboxyethylamino)benzaldehyde |
| 52 | 12, 13, 14 | 4-(Carboxymethylamino)benzaldehyde |
| 53 | 12, 13 | 4-(5-Carbomethoxypentylamino)benzaldehyde |
| 54 | 12, 13, 14 | 4-(1-Carboxybutylamino)benzaldehyde |
| 55 | 12, 13 | 4-(13-Carboethoxytridecylamino)benzaldehyde |
| 56 | 12, 13 | 4-(2-Carbomethoxyethylamino)benzaldehyde |
| 57 | 12, 13, 14 | 4-(10-Carboxydecylamino)benzaldehyde |
| 58 | 16 | Ethyl 4-(5-sulfopentylamino)benzoate |
| 59 | 16, 17 | 4-(11-Sulfoundecylamino)benzoic acid |
| 60 | 16, 17 | 4-(6-Sulfohexylamino)benzoic acid |
| 61 | 16, 17 | 4-(16-Sulfohexadecylamino)benzoic acid |
| 62 | 16 | Ethyl 4-(4-sulfoethylamino)benzoate |
| 63 | 15 | Ethyl 4-[6-(N-phenylsulfamyl)hexylamino]benzoate |
| 64 | 15 | Ethyl 4-[1-(N-methylsulfamyl)butylamino]benzoate |
| 65 | 15 | 4-[11-(N-ethylsulfamyl)undecylamino]benzoic acid |

TABLE I-continued

| Example No. | Method of Example | Compound |
|---|---|---|
| 66 | 15 | 4-[2-(N-methylsulfamyl)ethylamino]benzoic acid |
| 67 | 15 | 4-[6-(N-phenylsulfamyl)hexylamino]benzoic acid |
| 68 | 15 | Ethyl 4-[16-(N-methylsulfamyl)hexadecylamino]benzoate |
| 69 | 15 | Ethyl 4-{6-[N-(p-toluene)sulfamyl]hexylamino}benzoate |
| 70 | 15 | 4-[(N-methylsulfamyl)methylamino]benzoic acid |
| 71 | 12 | 4-(5-Carbomethoxyhexylamino)benzamide |
| 72 | 12 | 1-[4-(10-Carbomethoxydecylamino)benzoyl]pyrrolidine |
| 73 | 12 | 1-[4-(2-Carboethoxyethylamino)benzoyl]piperidine |
| 74 | 12 | 1-[4-(Carboethoxymethylamino)benzoyl]morpholine |
| 75 | 12 | 1-[4-(5-Carbomethoxypentylamino)benzoyl]pyrrolidine |
| 76 | 8 | Ethyl 4-(10-carbomethoxydec-9-enylamino)benzoate |
| 77 | 9 | 4-(15-carboxyentadeo-9-enylamino)benzoic acid |
| 78 | 18 | 4-(3-Carbomethoxyprop-2-enylamino)benzoic acid |
| 79 | 11 | Ethyl 4-(6-carboxyhex-5-enylamino)benzoate |
| 80 | 10 | Sodium 4-(15-carbomethoxypentadec-4-ynylamino)benzoate |
| 81 | 12, 14 | 4-(10-Carboethoxydec-9-enylamino)benzaldehyde |
| 82 | 12, 13, 14 | 4-(3-Carboxyprop-2-enylamino)benzaldehyde |
| 83 | 16, 17 | 4-(3-Sulfoprop-2-enylamino)benzoic acid |
| 84 | 16 | Ethyl 4-(11-sulfoundec-10-enylamino)benzoate |
| 85 | 15 | Ethyl 4-(15-methylsulfamylpentadec-4-ynylamino)benzoate |
| 86 | 15 | 4-[3-(N-Phenylsulfamyl)prop-2-enylamino)benzoic acid |
| 87 | 8 | Ethyl 4-[(3-carboethoxy-2,4,4-trimethylcyclohexyl)amino)benzoate |
| 88 | 11 | Ethyl 4-[(3-Carboxymethyl-2,2,4-trimethylcyclopentyl)amino]benzoate |

EXAMPLE 89

Preparation of 4(15-carbomethoxypentadecylamino)benzoyl chloride hydrochloride

A cold solution of 25 g. of 4(15-carbomethoxypentadecylamino)benzoic acid in 500 ml. of dimethoxyethane-methylene chloride (4:1) is prepared and dry hydrochloric acid is bubbled through the solution until no more precipitate forms. The solution is treated with 25 ml. of thionyl chloride and refluxed until all of the precipitate has redissolved. The solvents are evaporated to yield an orange, semi-crystalline mass.

EXAMPLE 90

Preparation of N-trifluoroacetyl-4-(15-carbomethoxypentadecylamino)benzoyl chloride To a stirred, ice-cold suspension of 9 g. 4-(15-carbomethoxypentadecylamino)benzoic acid in 100 ml. dimethoxyethane and 16 ml. pyridine is added 18 ml. trifluoroacetic anhydride. The solution is stirred at 0° C. for 30 minutes. The solution is diluted with 300 ml. ether and 100 g. ice. After stirring vigorously for 15 minutes, the phases are separated, the ether solution is washed with brine, dried and evaporated to a white, amorphous solid.

To 9.2 g. of the above product in 30 ml. methylene chloride and 0.5 ml. dimethylformamide is added 5.7 ml. thionyl chloride. After 20 hours at reflux, the solvents are evaporated to yield a light yellow, mobile oil.

EXAMPLE 91

Preparation of N-carbobenzyloxy-4-(15-carbomethoxypentadecylamino)benzoyl chloride To 15 g. of 4-(15-carbomethoxypentadecylamino)benzoic acid in 200 ml. warm chloroform is added 15 g. sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaporated to an oil. The oil is disolved in 300 ml. toluene, treated with 15 ml. of thionyl chloride, and the solution is refluxed for 5 hours. The solvents are evaporated and the residue is dissolved three times in toluene, evaporating each time to yield a viscous, orange oil.

EXAMPLE 92

Preparation of 1-{4-[N-(t-butyloxycarbonyl)-N-(15-carbomethoxypentadecyl)amino]benzoyl}imidazole A solution of 10 g. of 4-(15-carbomethoxypentadecylamino)benzoic acid in 100 ml. dioxane is treated with 4.0 g. of t-butylazidoformate and 10 ml. pyridine. After stirring at room temperature for 18 hours, the protected amido-acid is precipitated from solution by addition of 150 ml. of water. The product is collected and thoroughly dried. The crude product is dissolved in 200 ml. of a mixture consisting of methylene chloride/dimethoxyethane/pyridine (1:4:1), and to this is added 5.4 g. of 1,1'-carbonyldiimidazole. The solution is stirred overnight at room temperature and the solvents are evaporated to yield the title compound as a thick, orange oil.

EXAMPLE 93

Preparation of potassium sulfomethyl 4-(15-cabomethoxypentaamino)benzoate

To 39.3 g. of potassium 4-(15-carbomethoxypentadecylamino)benzoate in 125 ml. of hexamethylphosphoramide is added 26.0 g. of powdered potassium iodomethanesulfonate. After stirring for 24 hours at 25° C., the product is obtained by careful dilution with water or alcohol to the crystallization point.

When this reaction is carried out with potassium 2-iodoethanesulfonate, the potassium sulfoethyl ester is obtained.

EXAMPLE 94

2.3-Dihydroxypropyl 4-(15-carbomethoxypentadecylamino)benzoate

A solution of 7.34 g. of 4-(15-carbomethoxypentadecylamino)benzoic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 4-(15-carbomethoxypentadecylamino)benzoate.

EXAMPLE 95

2,3-Dihydroxypropyl 4-(15-carbomethoxypentadecylamino)benzoate

A solution of 11.8 g. of 4-(15-carbomethoxypentadecylamino)benzoic acid, 1.00 g. of glycerol, and 5.35 ml. of boron trifluoride etherate in 200 ml. of toluene is stirred under reflux for 4 hours. The solution is treated with an additional 5.35 ml. of boron trifluoride etherate and refluxing is continued for 120 hours. Dilution with water and methylene chloride followed by filtration affords 2,3-dihydroxypropyl 4-(15-carbomethoxypentadecylamino)benzoate as a white solid.

EXAMPLE 96

2,3-Dihydroxypropyl 4-(15-carbomethoxypentadecylamino)benzoate

A mixture of 2.25 g. of methyl 4-(15-carbomethoxypentadecylamino)benzoate, 280 mg. of glycerol, and 1.37 g. of p-toluenesulfonic acid is heated at 180° C. for 4 hours and then is partitioned between ether and 3% aqueous sodium carbonate solution. The ether layer is separated, dried, and evaporated to yield 2,3-dihydroxypropyl 4-(15-carbomethoxypentadecylamino)benzoate.

EXAMPLE 97

Methyl 4-(15-carbomethoxypentadecylamino)benzoate

A solution of 50.5 g. of 4-(15-carbomethoxypentadecylamino)benzoic acid and 34.4 ml. of boron trifluoride etherate in 200 ml. of methanol is stirred under reflux for 4 hours, allowed to cool, and is poured into 1.20 liters of ice cold 5% aqueous sodium carbonate solution. The white solid is collected by filtration and recrystallized from benzene-ethanol to yield methyl 4-(15-carbomethoxypentadecylamino)benzoate, m.p. 92°–93° C.

EXAMPLE 98

Preparation of 1-(methoxycarbonyl)propyl 4-(15-carbomethoxypentadecylamino)benzoate To a solution of 10.0 g. 4-(15-carbomethoxypentadecylamino)benzoyl chloride hydrochloride in 200 ml. methylene chloride is added dropwise a solution of 3 g. methyl α-hydroxy butyrate and 5 g. triethylamine in 100 ml. ether. After 17 hours stirring at room temperature, the precipitate is filtered and washed with several portions of ether. The ether solution is washed with water, dried, and condensed to the crystalline title compound.

EXAMPLE 99

Preparation of 1-carboxyethyl 4-(15-carbomethoxypentadecylamino)benzoate

A flask containing 10.0 g. 4-(15-carbomethoxypentadecylamino)benzoic acid, 3.3 g. lactic acid, 500 mg. toluene-sulfonic acid and 500 ml. toluene is equipped with a Soxhlet extractor charged with activated 4Å Linde molecular sieves. The solution is refluxed for 4 hours, during which time the Soxhlet extractor is charged twice more with fresh sieves. The hot solution is filtered and left to cool, whereupon the product separates as off-white crystals.

EXAMPLE 100

Preparation of diethyl O-[4-(15-carbomethoxypentadecylaminobenzoyl]tartarate

N-Trifluoroacetyl-4-(15-carbomethoxypentadecylamino)benzoyl chloride and 1.2 g. triethylamine in 100 ml. warm ether is treated with 2.5 g. diethyl tartarate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the diethyl tartarate as a white, crystalline solid.

EXAMPLE 101

Preparation of O-[4-(15-carbomethoxypentadecylamino)benzoyl]malic acid

To a warm solution of N-carbobenzyloxy-4-(15-carbomethoxypentadecylamino)benzoyl chloride and 1.3 g. triethylamine in 100 ml. ether is added 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, the solution is evaporated, and the residue is crystallized from acetic acid to yield the title compound as a tan, crystalline mass.

EXAMPLE 102

Preparation of 2-(ethoxycarbonyl)vinyl 4-(15-carbomethoxypentadecylamino)benzoate To a mixture containing 4.3 g. 1-{4-[N-(t-butyloxycarbonyl)-N-(15-carbomethoxypentadecyl)amino]benzoyl}imidazole, 50 ml. chloroform, and 50 ml. 5 N sodium hydroxide is added 3 g. ethyl α-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 4-(15-carbomethoxypentadecylamino)benzoate.

EXAMPLE 103

Preparation of 2-(ethoxycarbonyl)ethyl 4-(15-carbomethoxypentadecylamino)benzoate A solution of 4 g. 2-(ethoxycarbonyl)vinyl 4-(15-carbomethoxypentadecylamino)benzoate and 400 mg. 10% palladium-on-carbon in 100 ml. tetrahydrofuran is hydrogenated at 50 psi until hydrogen uptake stops. The catalyst is filtered, the solution is evaporated, and the residue is crystallized from acetonitrile to yield 2-(ethoxycarbonyl)ethyl 4-(15-carbomethoxypentadecylamino)benzoate.

TABLE II

The 4-[(substituted-alkyl)amino]benzoate esters shown in the Table are prepared by the methods of Examples 93–104. The requisite benzoic acids or their derivatives are prepared by the methods of Examples 9–18 and 89–92.

TABLE II

| Example No. | Method of Example | Compound |
|---|---|---|
| 104 | 94 | Isopropyl 4-(5-carbomethoxypentylamino)benzoate |
| 105 | 94 | 2-Ethoxyethyl 4-[11-(N-phenylsulfamyl)undecylamino]benzoate |
| 106 | 94 | Isopropyl 4-(13-carboethoxypentadecylamino)benzoate |
| 107 | 93 | Potassium sulfomethyl 4-(13-carbomethoxytridecylamino)benzoate |
| 108 | 93 | Ethyl O-[4-(10-carboethoxydec-2-enylamino)benzoyl]glycolate |
| 109 | 93 | 2-{4-[10-(Carbo-tert-butoxy)decylamino]benzoyl}ethanesulfonic acid |
| 110 | 93 | 2-[4-(5-carbomethoxypentylamino)benzoyl]ethanesulfonic acid |
| 111 | 93 | 2-[4-(2-carboethoxyethylamino)benzoyl]ethanesulfonic acid |
| 112 | 94 | 2,3-Dihydroxypropyl 4-(10-carbomethoxydecylamino)benzoate |
| 112a | 94 | 2,3-Dihydroxypropyl 4-(2-carbomethoxyethylamino)benzoate |
| 113 | 94 | 3-Hydroxypropyl 4-(2-carboethoxyethylamino)benzoate |
| 114 | 94 | 2,3-Dihydroxypropyl 4-(15-carbomethoxypentadec-4-ynylamino)benzoate |
| 115 | 94 | 2-Hydroxypropyl 4-[11-(N-phenylsulfamyl)undecylamino]benzoate |
| 116 | 94 | 2,3-Dihydroxypropyl 4-[2-(N-methylsulfamyl)ethylamino]benzoate |
| 117 | 95 | 2-Ethoxyethyl 4-(5-carbomethoxypentylamino)benzoate |
| 118 | 95 | Isopropyl 4-(15-carboethoxypentadecylamino)benzoate |
| 119 | 95 | 2-Dimethylaminoethyl 4-(10-carboethoxydec-9-enylamino)benzoate |
| 120 | 97 | Methyl 4-(2-carbophenoxyethylamino)benzoate |
| 121 | 97 | Methyl 4-(15-carbomethoxypentadec-4-ynylamino)benzoate |
| 122 | 97 | Methyl 4-[(3-carboxymethyl-2,2,4-trimethylcyclopentyl)amino]benzoate |
| 123 | 96 | 4-Hydroxybutyl 4-(2-carboethoxyethylamino)benzoate |
| 124 | 96 | 2-Ethoxyethyl 4-(15-carboethoxypentadecylamino)benzoate |
| 125 | 96 | 4-Methylbenzyl 4-(11-methylsulfamylundecylamino)benzoate |
| 126 | 98 | 1-Carbomethoxypropyl 4-(10-carbomethoxydec-9-enylamino)benzoate |
| 127 | 98 | Carbomethoxymethyl 4-(15-carbomethoxypentadecylamino)benzoate |
| 128 | 98 | 1-Carbomethoxypropyl 4-(5-carbomethoxypentylamino)benzoate |
| 129 | 98 | Carbomethoxymethyl 4-[(3-carbomethyoxy-2,4,4-trimethylcyclohexyl)amino] benzoate |
| 130 | 99 | 1-Carboxyethyl 4-[11-(N-phenylsulfamyl)undecylamino]benzoate |
| 131 | 99 | Carboxymethyl 4-[16-(N-methylsulfamyl)hexadecylamino]benzoate |
| 132 | 99 | 1-Carboxypropyl 4-(2-carbomethoxyethylamino)benzoate |
| 133 | 100 | 4-Pyridylmethyl 4-(10-carboethoxydec-9-enylamino)benzoate |
| 134 | 100 | 1-Methyl-4-piperidyl 4-(5-carboethoxypentylamino)benzoate |
| 135 | 100 | Diethyl O-[4-(5-carbomethoxypentylamino)benzoyl]tartarate |
| 136 | 100 | Diethyl O-[4-(15-carboethoxypentadecylamino)benzoyl]tartarate |
| 137 | 101 | O-{4-[11-(N-Phenylsulfamyl)undec-2-enylamino]benzoyl}malic acid |
| 138 | 101 | O-[4-(1-Carbomethoxybutylamino)benzoyl]malic acid |
| 139 | 101 | O-{4-[2-(N-Methylsulfamyl)ethylamino]benzoyl}tartaric acid |
| 140 | 102 | 2-(Ethoxycarbonyl)vinyl 4-(10-carbophenoxydec-9-enylamino)benzoate |
| 140 | 102 | 2-(Methoxycarbonyl)vinyl 4-[16-(N-methylsulfamyl)hexadecylamino]benzoate |
| 141 | 102 | 2-(Ethoxycarbonyl)vinyl 4-(5-carboethoxypentylamino)benzoate |
| 142 | 103 | 2-(Ethoxycarbonyl)ethyl 4-(1-carboethoxybutylamino)benzoate |
| 143 | 103 | 2-(Ethoxycarbonyl)ethyl 4-[(3-carboethoxy-2,2,4-trimethylcyclopentyl)amino]benzoate |

EXAMPLE 144

Preparation of 1-[4-(15-carbomethoxypentadecylamino)benzoyl]-piperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-(15-carbomethoxypentadecylamino)benzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with 100 ml. portions of water and dried over magnesium sulfate. The solvent is removed in vacuo and the solid is recrystallized in 50 ml. of diethyl ether to yield the product.

EXAMPLE 145

Preparation of ethyl 4-(15-carbomethoxypentadecylamino)hippurate

To a solution of 18.08 g. of 4-(15-carbomethoxypentadecylamino)benzoic acid in a mixture of dioxane and methylene chloride (40 ml./160 ml.) is added gaseous hydrogen chloride for 10 minutes. The slurry is cooled and 18 ml. of thionyl chloride added. The slurry is heated under reflux for 2 hours and then concentrated. The amber solution is diluted with 100 ml. of dioxane and then added to freshly prepared ethyl glycinate in 300 ml. of methylene chloride containing 1 g. of dimethylaminopyridine and 10 ml. of triethylamine. After 16 hours at room temperature the mixture is refluxed for 2 hours, cooled and filtered. The mother liquor is extracted with water and 10% hydrochloric acid. The solution is dried over magnesium chloride and concentrated in vacuo to an amber liquid. This material is chromatographed on a silica column and then recrystallized from acetonitrile to yield the product.

EXAMPLE 146

Preparation of N-[4-(15-carbomethoxypentadecylamino)benzoyl]glycine

A mixture of 26.4 g. of ethyl N-[4-(15-carbomethoxypentadecylamino)benzoyl]glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone to yield the product.

EXAMPLE 147

Preparation of p-(15-carbomethoxypentadecylamino)-N-(methylsulfonyl)benzamide

A solution of 19.0 g. of methanesulfonamide in 150 ml. of dry dimethylacetamide is added dropwise during 15 minutes to a stirred and cooled (water bath) suspension of 5.5 g. of sodium hydride in 100 ml. of dry dimethylacetamide. The mixture is then stirred and heated at 60°–80° C. for 2 hours. In the meantime, a mixture of 36.2 g. of p-(15-carbomethoxypentadecylamino)benzoic acid in 1200 ml. of methylene chloride, 300 ml. of dimethoxyethane and 40 ml. of thionyl chloride is refluxed for 1 hour and 15 minutes. The solution is evaporated to an oil which is coevaporated twice with added dioxane to remove excess thionyl chloride. To the resulting oily residue p-(15-carbomethoxypentadecylamino)benzoyl chloride hydrochloride is added, in one portion, the previously prepared mixture of sodium methanesulfonamide in dimethylacetamide. The mixture becomes very hot and is cooled briefly in a water bath and then is stirred at room temperature for 30 minutes. The mixture is filtered through a bed of diatomaceous earth and the filtrate is poured into 2 l. of water. The resulting suspension is coagulated by the addition of 250 ml. of saturated sodium chloride solution and the mixture is filtered. The product is washed with water, partially air dried and then crystallized from 1.5 l. of ethanol. The product is recrystallized from p-dioxane and dried at 65° C. to yield the title compound as tan crystals.

EXAMPLE 148

Preparation of [4-(15-carbomethoxypentadecylamino)benzoyl]hydroxamic acid

A solution of 16.7 g. of 4-(15-carbomethoxypentadecylamino)benzoyl chloride hydrochloride in methylene chloride is added at 5° C. to a mixture of 2.8 g. of hydroxyamine hydrochloride, 4.2 g. of sodium carbonate, and 120 ml. of ether. Water (10 ml.) is added and the mixture is stirred 3 hours. After the addition of 150 ml. of water, the solvents are evaporated. The crystalline residue is recrystallized from acetonitrile.

EXAMPLE 149

Preparation of 3-[4-(15-carbomethoxypentadecylamino)benzoyl]-4-carboxythiazolidine One-tenth mole of 4-(15-carbomethoxypentadecylamino)benzoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile to yield 3-[4-(16-bromohexadecylamino)benzoyl]-4-carbethoxythiazolidine. By means of the alkaline hydrolysis method of Example 10, the ethyl ester is converted to the subject carboxylic acid. This acid is also prepared using the procedure of this Example except that the acylation of the thiazolidine-4-carboxylic acid is carried out in aqueous acetone sodium bicarbonate solution.

EXAMPLE 150

Preparation of N-[4-(15-carbomethoxypentadecylamino)benzoyl]alanine

A solution of 4.75 g. of N-trifluoroacetyl-4-(15-carbomethoxypentadecylamino)benzoyl chloride and 1.2 g. of triethylamine in 20 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white, crystalline solid.

EXAMPLE 151

Preparation of 1-[4-(15-carbomethoxypentadecylamino)benzoyl]pyrrolidine

A solution of 6.0 g. of 4-[N-carbobenzyloxy-N-(15-carbomethoxypentadecylamino)benzoyl chloride and 1.2 g. triethylamine in 100 ml. warm ether is treated with 1.1 g. of pyrrolidine. After 1 hour at reflux, the precipitate is filtered and washed with warm ether. After evaporation to dryness, the intermediate is dissolved in 50 ml. 30% hydrobromic/acetic acid and warmed at 50° for 2 hours. The solvents are evaporated and the product is partitioned between methylene chloride and water. The layers are separated and the methylene chloride is evaporated. The residue is crystallized from acetone to yield colorless crystals.

EXAMPLE 152

Preparation of 4-(15-carbomethoxypentadecylamino)-N-(2,3-dihydroxypropyl)benzamide To a mixture containing 4.3 g. of 1-{4-[N-(t-butyloxycarbonyl)-N-(15-carbomethoxypentadecyl)amino]benzoyl}imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. and 50 ml. of anhydrous trifluoroacetic acid. The solvent is again evaporated and the oil is crystallized from acetone to yield the product as a light yellow crystalline solid.

TABLE III

The 4-[(substituted-alkyl)amino]benzamides shown in the Table are prepared by the methods of Examples 144–152. The requisite benzoic acids or their derivatives are prepared by the methods of Examples 9–18 and 89–92.

TABLE III

| Example No. | Method of Example | Compound |
|---|---|---|
| 153 | 152 | N-(2,3-Dihydroxypropyl)-4-(13-carbomethoxytridecylamino)benzamide |
| 154 | 152 | N-(2,3-Dihydroxypropyl)-4-[11-(N-methylsulfamyl)undecylamino]benzamide |
| 155 | 153 | N-(2-Hydroxypropyl)-4-(16-carbomethoxyhexadecylamino)benzamide |
| 156 | 144 | 1-[4-(10-Carbomethoxydecylamino)benzoyl]piperidine |
| 157 | 144 | 1-[4-(15-Carbomethoxypentadec-4-ynylamino)benzoyl]pyrrolidine |
| 158 | 144 | 1-[4-(2-Carbomethoxyethylamino)benzoyl]morpholine |
| 159 | 144 | 1-[4-(6-Carboethoxypentylamino)benzoyl]pyrrolidine |
| 160 | 145 | Ethyl 4-[11-(N-methylsulfamyl)undec-2-enylamino]hippurate |
| 161 | 145 | Ethyl 4-[(1-carboethoxybutylamino)hippurate |
| 162 | 145 | Ethyl 4-(2-carbomethoxyethylamino)hippurate |
| 163 | 146 | N-{4-[11-(N-phenylsulfamyl)undecylamino]benzoyl}glycine |
| 164 | 146 | N-[4-(15-carboxypentadecylamino)benzoyl]glycine |
| 165 | 146 | N-[4-(2-carboxyethylamino)benzoyl]glycine |
| 166 | 146 | N-[4-(1-carboxybutylamino)benzoyl]glycine |
| 167 | 146 | N-{4-[11-(N-Phenylsulfamyl)undec-2-enylamino]benzoyl}glycine |
| 168 | 147 | N-Methyl-4-(10-carbomethoxydecylamino)benzamide |
| 169 | 147 | N-Phenyl-4-(15-carbomethoxypentadecylamino)benzamide |
| 170 | 147 | N-(Methylsulfonyl)-4-(2-carbomethoxyethylamino)benzamide |
| 171 | 147 | N-(Phenylsulfonyl)-4-[(3-carbomethoxy-2,2,4-trimethylcyclopentyl)amino]benzamide |
| 172 | 148 | 4-[16-(N-Methylsulfamyl)hexadecylamino]benzoylhydroxamic acid |
| 173 | 148 | 4-(1-Carbomethoxybutylamino)benzoylhydroxamic acid |
| 174 | 148 | 4-(Carboxymethylamino)benzoylhydroxamic acid |
| 175 | 150 | 3-{4-[11-(N-Phenylsulfamyl)undec-2-enylamino]benzoyl}-4-carboxythiazolidine |
| 176 | 150 | 3-{4-[15-(Carboxypentadec-4-enyl)amino]benzoyl}-4-carboxythiazolidine |
| 177 | 150 | 3-[4-(5-Carboxypentylamino)benzoyl]-4-carboxythiazolidine |
| 178 | 151 | 1-[4-(16-Methylsulfamylhexadecylamino)benzoyl]piperidine |
| 179 | 151 | 1-[4-(Carboxymethylamino)benzoyl]pyrrolidine |
| 181 | 151 | 1-[4-(10-Carbomethoxydec-9-enylamino)benzoyl]pyrrolidine |
| 182 | 152 | N-(2,3-Dihydroxypropyl)-4-(10-carboethoxydecylamino)benzamide |
| 183 | 153 | N-(2,3-Dihydroxypropyl)-4-[11-(N-phenylsulfamyl)undec-2-enylamino]benzamide |

I claim:

1. A compound of the formula:

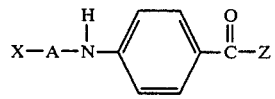

wherein X is selected from the group consisting of carboxy, lower alkoxycarbonyl and aryloxycarbonyl; A is an unbranched or branched alkylene group optionally saturated or mono- or poly-unsaturated, and containing or not containing a cycloalkyl group, represented by the formula $C_nH_{2(n-p)}$ with n being an integer from 8 to 18, inclusive, and p being an integer from 0 to 5, inclusive; and Z is selected from the group consisting of hydroxy, lower alkoxy, lower alkoxyalkoxy, di(lower alkyl)aminoalkoxy, (mono- or poly-hydroxy)lower alkoxy, allyloxy and substituted or unsubstituted benzyloxy; and the pharmaceutically acceptable non-toxic acid-addition and cationic salts thereof.

2. The compound 4-(15-carbomethoxypentadecylamino)benzoic acid.

3. The compound ethyl 4-(15-carbomethoxypentadecylamino)benzoate.

4. The compound 4-(10-carboxydecylamino)benzoic acid.

5. The compound 4-(15-carboxypentadecylamino)benzoic acid.

* * * * *